United States Patent [19]

Grand

[11] 3,940,482

[45] Feb. 24, 1976

[54] SOLUBILIZATION OF THE ZINC SALT OF 1-HYDROXY-2-PYRIDINETHIONE

[75] Inventor: Paul Sheldon Grand, South Bound Brook, N.J.

[73] Assignee: Colgate-Palmolive Company, New York, N.Y.

[22] Filed: Aug. 17, 1973

[21] Appl. No.: 389,326

Related U.S. Application Data

[62] Division of Ser. No. 136,204, April 2, 1971, Pat. No. 3,785,985.

[52] U.S. Cl. .................................. 424/245; 424/325
[51] Int. Cl.² .................................. A61K 31/555
[58] Field of Search ............................ 424/245, 325

[56] References Cited
UNITED STATES PATENTS

| | | | |
|---|---|---|---|
| 3,003,970 | 10/1961 | Call | 252/544 X |
| 3,108,036 | 10/1963 | Molnar | 424/347 |
| 3,580,853 | 5/1971 | Parran | 252/544 |
| 3,636,213 | 1/1972 | Gerstein et al. | 424/245 |
| 3,785,985 | 1/1974 | Grand | 252/106 |

OTHER PUBLICATIONS

Remington's Pharmaceutical Sciences, 13 ed. 1965, p. 1380.

*Primary Examiner*—Leonard Schenkman
*Attorney, Agent, or Firm*—Richard N. Miller; Ronald S. Cornell; Herbert S. Sylvester

[57] ABSTRACT

This invention relates to improved methods of solubilizing heavy metal salts of 1-hydroxy-2(1H)- pyridinethione. More particularly, the invention relates to solubilizing heavy metal salts of 1-hydroxy-2(1H) pyridinethione with polyamines and to compositions containing the solubilized salts.

9 Claims, No Drawings

SOLUBILIZATION OF THE ZINC SALT OF 1-HYDROXY-2-PYRIDINETHIONE

This is a divisional of application Ser. No. 136,204 filed Apr. 2, 1971, now U.S. Pat. No. 3,785,985.

This invention relates to improved methods of solubilizing heavy metal salts of 1-hydroxy-2(1H)-pyridinethione. More particularly, the invention relates to solubilizing heavy metal salts of 1-hydroxy-2(1H) pyridinethione with polyamines and to compositions containing the solubilized salts. A further aspect of this invention is the enhancement of the deposition of the heavy metal salts on skin or textiles.

The structural formula for 1-hydroxy-2(1H) pyridinethione (hereinafter referred to as pyridinethione) is shown below in tautomeric form, the sulfur being attached to the number 2 position of the pyridine ring:

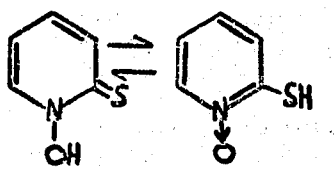

The heavy metal salts of pyridinethione are complexes of the heavy metal and pyridinethione.

The heavy metal salts of pyridinethione are described in detail in U.S. Pat. No. 2,809,971. As there reported, the heavy metal salts of pyridinethione can be prepared by a method which comprises interacting a soluble salt of pyridinethione (e.g. alkali metal or ammonium salt thereof) with a soluble compound of the desired heavy metal. On combination of these reactants, the metal salt precipitates and is recovered. Heavy metal compounds described as suitable reactants include, among others, copper, iron, manganese, tin, mercury, cobalt, chromium, lead, gold, cadmium, nickel, silver, titanium, arsenic, antimony, bismuth, zinc and zirconium. The term heavy metal as employed herein includes heavy non-metals of metallic character, e.g., arsenic, and these are characterized in the aforementioned patent as semi-metals. Preferred heavy metal salts of pyridinethione are zinc, cadmium and zirconium.

The heavy metal salts of pyridinethione are active bactericides and fungicides and certain of them are particularly adaptable to application to skin, hair and textiles.

Zinc omadine specifically is very effective as a dandruff controlling agent in shampoos and has found wide acceptance in the cosmetic and pharmaceutical arts for use in soaps, shampoos, hairdressings, tonics, rinses, lotions, ointments, salves and others. Some other uses of the zinc salt are as a biologically active agent for cutting oils and coolant systems, as an agent for protecting cellulosic fibers from loss of tensile strength due to action of fungi, and as a preservative for water based paints.

One disadvantage of the heavy metal salts of pyridinethione, such as the zinc salt, is their insolubility in common solvents. The zinc salt, for example, is substantially insoluble in water (10–20 ppm), ethanol (310 ppm), benzene (3–5 ppm), petroleum oils, and most common organic solvents such as ethylene glycol, diethyl ether and isopropanol. The material is slightly more soluble in chloroform (3400 ppm), dimethyl formamide (8100 ppm), and dimethyl sulfoxide (5.13 percent). Accordingly, it has been found difficult to formulate suitable cosmetic, textile treating and other compositions containing these heavy metal salts in dissolved form. The few solvents known for the salts are unacceptable especially for cosmetic and textile treating uses and the salts must always be present in such compositions in dispersed form, necessarily rendering the compositions opaque and causing precipitation problems.

It has been suggested that these heavy metal salts can be solubilized in common organic solvents and/or water by combining these salts with an amine or polyalkyleneimine. These compounds have been found to be ineffective in solubilizing the heavy metal salts of pyridinethione as demonstrated below by Examples 9 to 11.

The present invention overcomes the disadvantages of prior-art compositions and inadequacies of prior-art methods. Broadly, the present invention relates to a method of solubilizing heavy metal salts of 1-hydroxy-2(1H)-pyridinethione in water, detergent containing compositions, common organic solvents or mixtures thereof which comprises incorporating aliphatic polyamines of the general formula $H_2N(CH_2CH_2NH)_nH$ wherein $n$ represents a number from 1 to about 5, into compositions containing heavy metal salts of 1-hydroxy-2(1H)-pyridinethione. An additinoal advantage of the present invention is that it increases the deposition of heavy metal salts of pyridinethione on substrates such as gelatin, skin and textiles.

In general the compositions of this invention comprises base materials selected from the group consisting of water, organic detergent, common organic solvents and mixtures thereof; heavy metal salts of 1 hydroxy-2(1H) pyridinethione and aliphatic polyamines having the general formula described above.

The zinc salt of pyridinethione is soluble in water only to the extent of 6 ppm. However, as the pH is increased the solubility of the zinc salt increases being 35 ppm at a pH of 8. According to the present invention, however, the solubility of the zinc salt in compositions containing the described aliphatic polyamines and having a pH of about 9.0 or above is as high as about 100,000 ppm or more.

Because of the present inventions many clear products containing heavy metal salts of pyridinethione are now achievable. Examples of these are clear liquid antidandruff shampoo, clear soluble antidandruff hair groomers, clear soluble antibacterial skin cleansers, soluble substantive phytoxic agents, soluble antibacterial agents to treat textiles and disposable products, to mention a few.

The prior art warns that incorporating the zinc salt of pyridinethione into formulations containing sequestering agents such as for example ethylenediamine tetraacetic acid [$(HOOCCH_2)_2-N-CH_2CH_2-N-(CH_2COOH)_2$] and its salts has a very deleterious effect on the biocidal activity of this salt. Less than one part ethylenediamine tetraacetic acid per part pyridinethione salt will show this effect. However, in contradiction to the prior art warning, the aliphatic polyamines of the present invention, which are an important class of chelating compounds used as sequestering agents, do not decrease the biocidal activity and even a two-fold excess of a polyamine such as diethylene triamine does not reduce the antimicrobial activity of zinc pyridinethione.

Polyamines employable in the invention for solubilizing heavy metal pyridinethione salts are ethylene diamine (EDA) diethylene triamine (DETA) triethylene tetramine (TETA), tetraethylene pentamine (TEPA), and pentaethylene hexamine (PEHA).

The aliphatic polyamines will constitute a minor proportion of the compositions contemplated depending upon the amount of heavy metal salt of pyridinethione present. The ratio of aliphatic polyamine to pyridinethione heavy metal salt is generally about ½:1 to about 5:1. Preferably the ratio is about 1:1 to about 2:1.

In view of their antimicrobial effectiveness and of their substantivity, solubilized, pyridinethione heavy metal salts are particularly suitable for improving the condition of the hair, skin and textiles such as fabrics. More particularly, the solubilized salts may be incorporated into compatible cosmetic and textile treating vehicles to form cosemtic compositions for application to the hair and skin to improve the condition, including general health, thereof and textile treating compositions for application to textiles in particular fabrics rendering them sanitary.

By suitable selections of compatible cosmetic vehicles, it is contemplated that the present cosmetic compositions may be prepared in the form of daily skin or hair conditioning products such as skin lotions or hair conditioning rinses, daily hair-grooming products, such as hair lotions, hair sprays and dressings, hair tonics, and the like, or they may be prepared in the form of cleansing products, such as hair shampoos.

By suitable selections of compatible, textile treating vehicles, it is contemplated that present textile treating compositions may be prepared in the form of antibacterial compositions for treating fabrics, disposable products such as diapers, and cellulosic fibers to protect them from loss of tensile strength.

The heavy metal salts of pyridinethione will constitute generally a minor proportion, on the order of about ¼ percent to 20 percent by weight of the compositions, but the proportion will vary depending on the nature of the product. Generally concentrations of pyridinethione heavy metal salts in the range of ½ percent to 10 percent by weight of the composition are preferred for cosmetic and textile treating products. More preferred are concentrations of ½ percent to 5 percent, and most preferred are concentrations of ½ to 2 percent by weight of the total composition.

The vehicle accounts for the balance of about 99.25 percent to about 70 percent by weight of the cosmetic skin, and hair compositions, and textile treating compositions and its specific composition will vary according to the end use of the composition. The proportions of all vehicle compositions are expressed as percent by weight of the total composition.

The vehicle in liquid, hair- or skin-compositions may be water, common organic solvents or mixtures thereof. Suitable common organic solvents are $C_2$-$C_3$ lower monohydric or polyhydric alcohols such as ethanol, propanol, isopropanol, glycerine, dimethylformamide, dimethylacetamide, and dimethylsulfoxide, to mention a few.

In liquid hair-grooming compositions generally the vehicle will contain from about 0.5 percent to 65 percent and preferably 3 to 50 percent by weight of a non-volatile hairgrooming agent.

The balance of the vehicle will vary according to the form of the resultant product, and generally will be an aqueous medium, such as water or mixtures of water and a lower monohydric alcohol, such as ethanol or isopropanol. In the aqueous alcoholic mixtures, as little as 5 percent by weight of water may be present with the balance being lower alcohol. Generally water is about 30 percent to 80 percent by weight of the vehicle.

In liquid cleansing compositions, such as shampoos, and textile treating compositions, the vehicle will generally contain about 10 to 50 percent, preferably about 15 to 35 percent by weight of a compatible, water-soluble synthetic organic detergent and a balance of water and/or other components.

In the case of liquid cleansing compositions for the hair and skin, such as shampoo and textile treating compositions, suitable water-soluble synthetic, organic detergents may be selected from the group consisting of anionic, nonionic, amphoteric, zwitterionic, polar nonionic, and cationic detergents, and mixtures of two or more of the foregoing detergents.

The compatible anionic surface active agents include those surface active or detergent compounds which contain an organic hydrophobic group containing generally 8 to 26 carbon atoms and preferably 10 to 18 carbon atoms in their molecular structure, and at least one water-solubilizing group selected from the group of sulfonate, sulfate, carboxylate, phosphonate and phosphate so as to form a water-soluble detergent.

Examples of suitable anionic detergents which fall within the scope of the anionic detergent class include the water-soluble salts, e.g., the sodium, ammonium, and alkylolammonium salts, of higher fatty acids or resin salts containing about 8 to 20 carbon atoms, preferably 10 to 18 carbon atoms. Suitable fatty acids can be obtained from oils and waxes of animal or vegetable origin, e.g., tallow, grease, coconut oil, tall oil and mixtures thereof. Particularly useful are the sodium and potassium salts of the fatty acid mixtures derived from coconut oil and tallow, e.g., sodium coconut soap and potassium tallow soap.

The anionic class of detergents also includes the water-soluble sulfated and sulfonated synthetic detergents having an alkyl radical of 8 to 26, and preferably about 12 to 22 carbon atoms, in their molecular structure. (The term alkyl includes the alkyl portion of the higher acyl radicals.)

Examples of the sulfonated anionic detergents are the higher alkyl mononuclear aromatic sulfonates such as the higher alkyl benzene sulfonates containing from 10 to 16 carbon atoms in the higher alkyl group in a straight or branched chain, e.g., the sodium, potassium and ammonium salts of higher alkyl benzene sulfonates, higher alkyl toluene sulfonates, higher alkyl phenol sulfonates, and higher naphthalene sulfonates. A preferred sulfonate is linear alkyl benzene sulfonate having a high content of 3- (or higher) phenyl isomers and a correspondingly low content (well below 50 percent) of 2- (or lower) phenyl isomers, i.e., wherein the benzene ring is preferably attached in large part at the 3 or higher (e.g., 4, 5, 6 or 7) position of the alkyl group and the content of isomers is which the benzene ring is attached at the 2 or 1 position is correspondingly low. Particularly preferred materials are set forth in U.S. Pat. No. 3,320,174.

Other suitable anionic detergents are the olefin sulfonates, including long-chain alkene sulfonates, long-chain hydroxyalkane sulfonates or mixtures of alkenesulfonates and hydroxylalkane-sulfonates. These olefin sulfonate detergents may be prepared in a known manner by the reaction of $SO_3$ with long-chain olefins containing 8 to 25, preferably 12–21, carbon atoms and having the formula $RCH=CHR_1$ where R is a higher alkyl group of 6 to 23 carbons and $R_1$ is an alkyl group of 1 to 17 carbons or hydrogen to form a mixture of sultones and alkene-sulfonic acids which is then treated to convert the sultones to sulfonates. Other examples of sulfate or sulfonate detergents are paraffin sulfonates containing about 10–20, preferably about 15–20 carbon atoms, e.g., the primary paraffin sulfonates made by reacting long-chain alpha olefins and bisulfites and paraffin sulfonates having the sulfonate groups distributed along the paraffin chain as shown in U.S. Pat. Nos. 2,503,280; 2,507,088; 3,260,741; 3,372,188 and German Pat. No. 735,096; sodium and potassium sulfates of higher alcohols containing 8 to 18 carbon atoms such as sodium lauryl sulfate and sodium tallow alcohol sulfate; sodium and potassium salts of $\alpha$-sulfofatty acid esters containing about 10 to 20 carbon atoms in the acyl group, e.g., methyl $\alpha$-sulfomyristate and methyl $\alpha$-sulfo-tallowate, ammonium sulfates of mono- or di-glycerides of higher ($C_{10}$-$C_{18}$) fatty acids, e.g., stearic monoglyceride monosulfate; sodium and alkylolammonium salts of alkyl polyethenoxy ether sulfates produced by condensing 1 to 5 moles of ethylene oxide with one mole of higher ($C_8$-$C_{18}$) alcohol; sodium higher alkyl ($C_{10}$-$C_{18}$) glyceryl ether sulfonates; and sodium or potassium alkyl phenol polyethenoxy ether sulfates with about 1 to 6 oxyethylene groups per molecule and in which the alkyl radicals contain about 8 to about 12 carbon atoms.

The suitable anionic detergents include also the $C_8$-$C_{18}$ acyl sarcosinates (e.g. sodium lauroyl sarcosinate), sodium and potassium salts of the reaction product of higher fatty acids containing 8 to 18 carbon atoms in the molecule esterified with isethionic acid, and sodium and potassium salts of the $C_8$-$C_{18}$ acyl N-methyl taurides, e.g., sodium cocoyl methyl taurate and potassium stearoyl methyl taurate.

Anionic phosphate surfactants in which the anionic solubilizing group attached to the hydrophobic group is an oxyacid of phosphorous are also useful in the detergent compositions. Suitable phosphate surfactants are the sodium potassium and ammonium alkyl phosphate esters such as $(R-O)_2PO_2M$ and $ROPO_3M_2$ in which R represents an alkylchain containing from about 8 to about 20 carbon atoms or an alkyl phenyl group having 8 to 20 carbon atoms and M represents a soluble cation. The compounds formed by including about one to 40 moles of ethylene oxide in the foregoing esters, e.g. $[R-O(EtO)n]_2PO_2M$, are also satisfactory.

The particular anionic detergent salt will be suitably selected depending upon the particular formulation and the proportions therein. Suitable salts include the ammonium, substituted ammonium (mono-, di- and triethanolammonium), alkali metal (such as sodium and potassium) and alkaline earth metal (such as calcium and magnesium) salts. Preferred salts are the ammonium, triethanolammonium, sodium and potassium salts of the higher alkyl sulfates and the $C_8$-$C_{18}$ acyl sarcosinates.

The nonionic synthetic organic detergents are generally the condensation product of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a nonionic detergent. Further, the length of the polyethenoxy chain can be adjusted to achieve the desired balance between the hydrophobic and hydrophilic elements.

The nonionic detergents include the polyethylene oxide condensate of one mole of alkyl phenol containing from about 6 to 12 carbon atoms in a straight- or branched-chain configuration with about 5 to 30 moles of ethylene oxide, e.g., nonyl phenol condensed with 9 moles of ethylene oxide, dodecyl phenol condensed with 15 moles of ethylene oxide and dinonyl phenol condensed with 15 moles of ethylene oxide. Condensation products of the corresponding alkyl thiophenols with 5 to 30 moles of ethylene oxide are also suitable.

Still other suitable nonionics are the polyoxyethylene polyoxypropylene adducts of 1-butanol. The hydrophobe of these nonionics has a minimum molecular weight of 1,000 and consists of an aliphatic monohydric alcohol containing from 1 to 8 carbon atoms to which is attached a heteric chain of oxyethylene and oxypropylene. The weight ratio of oxypropylene to oxyethylene covers the range of 95:5 to 85:15. Attached to this is the hydrophilic polyoxyethylene chain which is from 44.4 to 54.6 percent of the total molecular weight of 1,400 to 4,000.

Also included in the nonionic detergent class are the condensation products of a higher alcohol containing about 8 to 18 carbon atoms in a straight or branched-chain configuration condensed with about 5 to 30 moles of ethylene oxide, e.g., lauryl-myristyl alcohol condensed with about 16 moles of ethylene oxide.

A particularly useful group of nonionics is marketed under the trade name "Pluronics." The compounds are formed by condensing ethylene oxide with a hydrophobic base formed by the condensation of propylene oxide with propylene glycol. The molecular weight of the hydrophobic portion of the molecule is of the order of 950 to 4000, preferably 1200 to 2500. The addition of polyoxyethylene radicals to the hydrophobic portion tends to increase the solubility of the molecule as a whole. The molecular weight of the block copolymers varies from 1100 to 15,000 and the polyethylene oxide content may comprise 20 to 80 percent by weight.

Other suitable nonionics may be derived by the condensation of ethylene oxide with the product resulting from the reaction of propylene oxide and ethylene diamine. The molecular weight varies from 500 to 4,500.

Other nonionic detergents include the ethylene oxide addends of monoesters of hexahydric alcohols and inner ethers thereof with higher fatty acids containing about 10 to 20 carbon atoms, e.g., sorbitan monolaurate, sorbitan mono-oleate, and mannitan monopalmitate.

The amphoteric detergents which can be used in the compositions of this invention are generally water-soluble salts of derivatives of aliphatic amines which contain at least one cationic group, e.g., non-quaternary nitrogen, quaternary ammonium, or quaternary phosphonium group, at least one alkyl group of about 8 to 18 carbon atoms and an anionic water-solubilizing carboxyl, sulfo, sulfato, phosphato or phosphono group in their molecular structure. The alkyl group may be straight chain or branched and the specific cationic atom may be part of a heterocyclic ring.

Examples of suitable ampholytic detergents include the alkyl beta-aminopropionates, $RN(H)C_2H_4COOM$; the alkyl betaiminodipropionates, $RN(C_2H_4COOM)_2$;

the alkyl and hydroxy alkyl taurinates, $RN(CH_3)C_2H_4SO_3M$; and the long-chain imidazole derivatives having the following formulas:

(I)
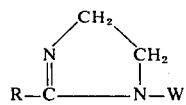

(II)
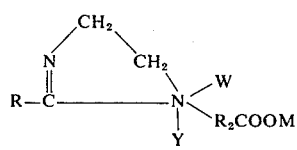

wherein R is an acyclic group of about 7 to 17 carbon atoms, W is selected from the group of R OH, $R_2COOM$, and $R_2OR_2COOM$, Y is selected from the group consisting of $OH^-$, $R_3OSO_3^-$, $R_2$ is an alkylene or hydroxyalkylene group containing 1 to 4 carbon atoms, R is selected from the group consisting of alkyl, alkyl aryl and fatty acyl glyceride groups having 6 to 18 carbon atoms in the alkyl or an acyl group; and M is a water-soluble cation, e.g., sodium potassium, ammonium or alkylolammonium.

Formula I detergents are disclosed in Volume II of "Surface Active Agents and Detergents" and in French Patent 1,412,921 and Formula II detergents are described in U.S. Pat. Nos. 2,773,068; 2,781,354, and 2,781,357. The acyclic groups may be derived from coconut oil fatty acids (a mixture fo fatty acids containing 8 to 18 carbon atoms), lauric fatty acid, and oleic fatty acid and the preferred groups are $C_7$-$C_{17}$ alkyl groups. Preferred detergents are sodium N-lauryl betaaminopropionate, disodium N-lauryl iminodipropionate, and the disodium salt of 2-lauryl-cycloimidium-1-hydroxyl, 1-ethoxy-ethanoic acid, 1-ethanoic acid.

Zwitterionic detergents such as the betaines and sulfo-betaines having the following formula are also useful:

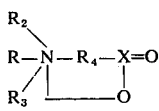

wherein R is an alkyl group containing about 10 to 18 carbon atoms, $R_2$ and $R_3$ are each $C_1$-$C_3$ alkyl, $R_4$ is an alkylene or hydroxyalkylene group containing about 1 to 4 carbon atoms, and X is C or S:O. The alkyl group can contain one or more intermediate linkages such as amido, either or polyether linkages or non-functional substituents such as hydroxyl or halogen which do not substantially affect the hydrophobic character of the group. When X is C, the detergent is called a betaine; and when X is S:O, the detergent is called a sulfobetaine or sultaine. Preferred betaine and sulfobetaine detergents are 1-(lauryl dimethyloammonio) acetate, 1-(myristyl dimethylammonio) propane-3-sulfonate, and 1-(myristyldimethylammonio)-2-hydroxypropane-3-sulfonate.

The polar nonionic detergents are those in which the hydrophilic group contains a semi-polar bond directly between two atoms, for example, N → O; P → O, As → O, and S → O. There is charge separation between the two directly bonded atoms, but the detergent molecule bears no net charge and does not dissociate into ions.

The polar nonionic detergents of this invention include open-chain aliphatic amine oxides of the general formula $R_1R_2R_3N \rightarrow O$. For the purposes of this invention $R_1$ is an alkyl, alkenyl, or monohydroxyalkyl radical having about 10 to 16 carbon atoms. $R_2$ and $R_3$ are each selected from the group consisting of methyl, ethyl, propyl, ethanol, and propanol radicals.

Other operable polar nonionic detergents are the openchain aliphatic phosphine oxides having the general formula $R_1R_2R_3P \rightarrow O$ wherein $R_1$ is an alkyl, alkenyl, or monohydroxyalkyl radical ranging in chain length from 10 to 18 carbon atoms, and $R_2$ and $R_3$ are each alkyl and monohydroxyalkyl radicals containing from 1 to 3 carbon atoms.

Cationic surface active agents may also be employed. Such agents are those surface active detergent compounds which contain an organic hydrophobic group and a cationic solubilizing group. Typical cationic solubilizing groups are amine and quaternary groups.

Examples of suitable synthetic cationic detergents are normal primary amines $RNH_2$ wherein R is $C_{12}$-$C_{15}$; the diamines such as those of the type $RNHC_2H_4NH_2$ wherein R is an alkyl group of about 12 to 22 carbon atoms, such as N-2-aminoethyl stearyl amine and N-2-aminoethyl myristyl amine; amidelinked amines such as those of the type $R_1CONHC_2H_4NH$ wherein $R_1$ is an alkyl group of about 8 to 20 carbon atoms, such as N-2-amino ethylstearyl amide and N-amino ethylmyristyl amide; quaternary ammonium compounds wherein typically one of the groups linked to the nitrogen atom is an alkyl group of about 8 to 22 carbon atoms and three of the groups linked to the nitrogen atom are alkyl groups which contain 1 to 3 carbon atoms, including alkyl groups bearing inert substituents, such as phenyl groups, and there is present an anion such as halogen, acetate, methosulfate, etc. The alkyl group may contain intermediate linkages such as amido which do not substantially affect the hydrophobic character of the group, e.g., stearyl amido propyl quaternary ammonium chloride. Typical quaternary ammonium detergents are ethyl-dimethyl-stearyl ammonium chloride, benzyl-dimethyl-stearyl ammonium chloride, trimethyl-stearyl ammonium chloride, trimethyl-cetyl ammonium bromide, dimethyl-ethyl-lauryl ammonium chloride, dimethylpropyl-myristyl ammonium chloride, and the corresponding methosulfates and acetates.

The cosmetic compositions for the hair and skin may also contain as adjuvant materials various substances, such as vitamins, lanolin, bacteriocides, plant extracts, coloring agents, perfumes, thickeners such as cellulose, opacifiers, and sequestering agents in order to enhance the cosmetic or antimicrobial properties of the resultant composition. Buffers may also be included to provide a suitable pH depending upon the nature of the proeuct prepared.

The hair, skin and textile treating compositions of the invention which contain solubilized heavy metal salts of pyridinethione are characterized by an outstanding ability to inhibit the growth of P. ovale, the yeast believed to be associated with dandruff. The aliphatic polyamine renders the active ingredient substantive (remain on the hair and skin) and therefore the period of time of bacteriostatic effect is extended.

The following examples further illustrate and describe the invention.

Examples 1–6 illustrate water and detergent compositions containing solubilized zinc 1-hydroxy-2(1H)-pyridinethione.

EXAMPLE 1

Biocidal Composition

| | |
|---|---|
| Zinc pyridinethione | 1.50% |
| Water | 95.50 |
| Diethylene triamine (DETA) | 3.00 |
| | 100.00% by weight |

To 0.75 g. of pyridinethione is added 47.75 g. water. This 48.5 g. slurry is stirred for 1 minute. To this slurry is added 1.5 g. of DETA. Zinc pyridinethione is completely dissolved. It is observed that mixing the aliphatic polyamine and the heavy metal salt before diluting with water results in a clear yellow solution. To obtain a clear colorless solution it is preferred to dilute either the aliphatic polyamine or the heavy metal salt of pyridinethiene with water or solvent prior to the addition of the other ingredient.

Similar results are obtained with other salts of pyridinethione, e.g., cadmium and zirconium salts.

Other suitable formulations productive of desired results are illustrated in Examples 2–4.

Example 2

| | Percent by Weight |
|---|---|
| Zirconium pyridinethione | 5.0% |
| Water | 75.0 |
| Tetraethylene/pentamine (TEPA) | 20.0 |
| | 100.0% |

Example 3

| | Percent by Weight |
|---|---|
| Zinc pyridinethione | 10.0% |
| Water | 40.0 |
| Diethylene triamine (DETA) | 50.0 |
| | 100.0% |

Example 4

| | Percent by Weight |
|---|---|
| Zinc pyridinethione | 20.0% |
| Water | 70.0 |
| Diethylene triamine (DETA) | 10.0 |
| | 100.0% |

Desired results are also obtained with similar formulations containing pentaethylene hexamine (PEHA) and ethylene diamine (EDA).

EXAMPLE 5

The following is an example of an anionic shampoo having biocidal activity:

| | Percent by Weight |
|---|---|
| Triethanolamine lauryl sulfate (TEALS) | 10.0% |
| Lauryl dimethylamine oxide (LDMAO) | 10.0 |
| Cocomonethanolamide (CMA) | 5.0 |
| Ethanol (ETOH) | 10.0 |
| Zinc pyridinethione | 1.5 |
| Diethylenetriamine (DETA) | 3.0 |
| Water | 60.5 |
| | 100.0% |

This shampoo is prepared as follows: To 1.5 g. zinc pyridinethione and 15.5 g. water is added 3.0 g. DETA. To this 20.0 g. solution of slurry is added 80 g. of the following anionic base: 24.20 g. TEALS (41.1% A.I.*), 33.70 g. LDMAO (29.65% A.I.), 5.0 g. CMA and 10.50 g. ETOH (95% A.I.) and 6.6 g. H₂O. This composition is prepared by combining TEALS, LDMAO, CMA and water at room temperature (20°–25°C.) heating with stirring to about 150°F., cooling to room temperature, adding ETOH and adjusting with water to 80 g. The base is combined and stirred at room temperature with zinc pyridinethione, water and DETA. A crystal clear shampoo results having biocidal activity.

*A.I. means active ingredient.

Desired results are also obtained with triethylene tetramine (TETA) as the solubilizing polyamine.

EXAMPLE 6

The following is an example of an amphoteric shampoo having biocidal activity:

| | Percent by Weight |
|---|---|
| $C_8$–$C_{18}$ alkyl amidopropyl dimethyl betaine (CADG) | 16.0% |
| Triethanolamine lauryl sulfate (TEALS) | 4.0 |
| Lauryl dimethylamine oxide (LDMAO) | 0.5 |
| Mixed polymer having a molecular weight of about 4000 formed by condensing a 1:1 mixture of ethylene oxide and propylene oxide on butanol (Ucon 50 HB 5100) | 2.00 |
| Resinous condensate of about 2 moles of epichlorohydrin and one mole of diethylene triamine having a molecular weight of about 80,000 | 0.50 |
| Polyoxypropylene-polyoxyethylene block copolymer wherein the hydrophobic group has a molecular weight of 1,750 and ethylene oxide is 20% by weight (Pluronic L62) | 5.00 |
| Ethanol (ETOH) | 2.00 |
| Zinc pyridinethione | 1.50 |
| Diethylenetriamine (DETA) | 3.00 |
| Water | 65.50 |
| | 100.00% |

This shampoo is prepared in the same manner described in Example 2. A crystal clear shampoo results.

EXAMPLE 7

The results of an experiment to show that the antimicrobial activity of zinc pyridinethione is maintained when the salt is solubilized by the aliphatic polyamines of this invention are disclosed in Table I.

The microbial effectiveness of compositions of the invention containing solubilized heavy metal salts of pyridinethione was determined using the "Test Tube Serial Dilution Method" described on pages 195–200 of the Fifth Edition of "Diagnostic Bacteriology" by Schaub et al. Table I sets forth the "minimum inhibitory concentration" (MIC) as determined using the aforementioned method against P. ovale of these compositions.

TABLE I

| Test Composition | MIC in micrograms per milliliter (μg/ml) against P. ovale |
|---|---|
| 1% diethylenetriamine in water | 500 → 1000 |
| 1% ethylene diamine in water | 500 → 1000 |
| 1% zinc pyridinethione in water | 1.9 → 7.8 |

TABLE I-continued

| Test Composition | MIC in micrograms per milliliter ($\mu$g/ml) against P. ovale |
|---|---|
| 1% zinc pyridinethione + 1% diethylenetriamine in water | 1.9 → 7.8 |

EXAMPLE 8

In addition to maintaining the antimicrobial activity of heavy metal salts of pyridinethione solubilized by the polyamines, enhanced deposition of zinc pyridinethione on substrates has been observed and is shown in Table II. Deposition was determined by stirring a half-inch diameter circular gelatin disk weighing about 40 milligrams in 10 grams of 1% by weight of radio-active (zinc-65 tagged) pyridinethione salt, rinsing the disk 5 times in 10 milliliters of water and measuring the radio-active emission with the aid of a radiation detector.

TABLE II

| Composition | Absolute Degree of Deposition ($\mu$g/disc) |
|---|---|
| Water + 1.5% zinc 65 pyridinethione | 40.9 |
| Water + 1.5% zinc 65 pyridinethione + 3% ethylene diamine | 181 |
| Water + 1.5% zinc 65 pyridinethione + 3% diethylenetriamine | 178 |
| Water + 1.5% zinc 65 pyridinethione + 3% tetraethylenepentamine | 181 |
| Shampoo of Example 5 without diethylenetriamine but the zinc is zinc 65 | 8.7 |
| Shampoo of Example 5 where zinc is zinc 65 | 45.9 |
| Shampoo of Example 5 where zinc is zinc 65 and diethylenetriamine is replaced by ethylene diamine | 23 |
| Shampoo of Example 6 where zinc is zinc 65 and diethylenetriamine is replaced by tetraethylenepentamine | 43.6 |

From Table II it is demonstrated that the addition of aliphatic polyamines to water and shampoos containing zinc pyridinethione results in depositions of zinc pyridinethione which are 3 to 21 times amount obtained when aliphatic polyamines. Similar increases in depositions are obtainable with amphoteric shampoos such as described in Example 6.

The experiments in Examples 9 to 11 compare the solubilizing agents suggested by the prior art to those of the present invention. These results show that the prior-art suggested solubilizing agents such as polyethyleneimine and diglycol amine are ineffective.

EXAMPLE 9

To 0.75 g. of zinc pyridinethione is added 47.75 g. $H_2O$. This 48.5 g. slurry is stirred for 1 minute. In two separate experiments, to this slurry is added 1.5 g. of diethylenetriamine (DETA) and diglycolamine (DGA). Also, to 0.75 g. zinc pyridinethione is added 44.75 g. $H_2O$. The 45.50 g. slurry is stirred for 1 minute. To this slurry is added 4.5 g. of polyethyleneimine (PEI-1000)* (33% A.I.**). So, in each of the three experiments there is 1.5% zinc pyridinethione and 3.0% solubilizer and balance is made up to 100% with water (95.5%). The visual observations of these solutions are recorded in Table III.

TABLE III

| Experimental Conditions | Visual Observations | | |
|---|---|---|---|
| | Preparation with DETA | Preparation with DGA | Preparation with PEI-1000 |
| Stirring at room temperature for 3 minutes | Complete solubility of zinc pyridinethione. | Less than 10% solubility of zinc pyridinethione. | Approximately 20% solubility of zinc pyridinethione. |
| Hot plate heating until 110°F. | Maintenance of solubility. | No greater solubility. Zinc pyridinethione quickly settles. | No greater solubility but zinc pyridinethione in uniform suspension. |
| Infinite dilution with $H_2O$ of clear solution | Solubility upon infinite dilution with water. No cloudiness developed. | | |
| pH of solution unadjusted | 11.5 | 11.2 | 9.3 |
| Adjusted pH downward with HCl | Start clouding up solution at approximately pH 9.2. Approximately 50% precipitation at pH 8.8. | Excessively less solubilization than above observed. | Excessively less solubilization than above observed. |

*PEI-1000 is a polymer of ethyleneimine with average molecular weight = 100,000 prepared by polymerization of ethyleneimine and containing a primary-, secondary-, tertiary- amine ratio of 1:2:1.
**A.E. means active ingredients.

The degree of solubilization of zinc pyridinethione by diethylenetriamine, diglycolamine and polyethyleneimine into both an anionic (Table IV) and amphoteric (TABLE VI) shampoo base was studied.

EXAMPLE 10

The following anionic shampoo systems are prepared:

TABLE IV

|  | Anionic I | Anionic II | Anionic III |
|---|---|---|---|
| Triethanolamine lauryl sulfate (TEALS) | 10.0% solids | 10.0% | 10.0% |
| Lauryl dimethylamine oxide (LDMAO) | 10.0 | 10.0 | 10.0 |
| Cocomonoethanol amide (CMA) | 5.0 | 5.0 | 5.0 |
| Ethanol (ETOH) | 10.0 | 10.0 | 10.0 |
| Zinc pyridinethione | 1.5 | 1.5 | 1.5 |
| Diethylenetriamine (DETA) | 3.0 | | |
| Diglycolamine (DGA) | | 3.0 | |
| Polyethyleneimine (PEI-1000) | | | 3.0 |
| $H_2O$ | 60.5 | 60.5 | 60.5 |
| | 100.0% | 100.0% | 100.0% |

The shampoos are prepared as follows: To 1.5 g. zinc pyridinethione and 15.5 g $H_2O$ (as in preparations I and II) or 9.5 g. $H_2O$ (as in preparation III) is added 3.0 g. DETA or 3.0 g. DGA or 9.0 g. (33% A.I.*) PEI-1000. To this 20.0 g. solution of slurry is added 80 g. of the following shampoo base: 24.20 g. TEALS (41.1% A.I.), 33.70 g. LDMAO (29.65% A.I.), 5.0 g. CMA and 10.50 g. ETOH (95% A.I.) and 6.6 g. $H_2O$. The shampoo base is prepared by combining TEALS, LDMAO, CMA and $H_2O$ at room temperature, heating with stirring to 150°F., cooling to room temperature, adding ETOH and adjusting with $H_2O$ to 80.0 g. The base was combined and stirred at room temperature with zinc pyridinethione and $H_2O$ and solubilizer (DETA, DGA or PEI-1000) combination.

*A.I. means Active Ingredient.)

The visual observations of these shampoo systems are recorded in Table V.

TABLE V

| Experimental Conditions | Visual Observations | | |
|---|---|---|---|
| | DETA | DGA | PEI-1000 |
| pH - unadjusted Visual - unadjusted | 9.75 Crystal clear shampoo. | 9.0 Cloudy shampoo, less than 10% zinc pyridinethione is soluble. | 8.6 Large quantity of gummy-like precipitate. |
| pH adjustment | Decrease pH with HCl pH 9.3 = pH 9.2 = pH 9.0 = pH 8.5 = | clear soluble system slightly cloudy cloudy with slight degree of precipitation cloudy yellow solution with precipitate | |

EXAMPLE 11

The following amphoteric shampoo systems are prepared:

TABLE VI

|  | Amphoteric I | Amphoteric II | Amphoteric III |
|---|---|---|---|
| Cocoamidepropyldimethyl betaine | 16.0% solids | 16.0 | 16.0 |
| Triethanolamine lauryl sulfate | 4.0 | 4.0 | 4.0 |
| Lauryl dimethylamine oxide | 0.5 | 0.5 | 0.5 |
| Mixed polymer having a molecular weight of about 4000 formed by condensing a 1:1 mixture of ethylene oxide and propylene oxide on butanol (Ucon 50 HB 5100) | 2.0 | 2.0 | 2.0 |
| Resinous condensate of about 2 moles of epichlorohydrin and one mole of diethylene triamine having a molecular weight of about 80,000 | 0.5 | 0.5 | 0.5 |
| Polyoxypropylene-polyoxyethylene block copolymer wherein the hydrophobic group has a molecular weight of 1,750 and ethylene oxide is 20% by weight (Pluronic L62) | 5.0 | 5.0 | 5.0 |
| Ethanol | 2.0 | 2.0 | 2.0 |
| Zinc pyridinethione | 1.5 | 1.5 | 1.5 |
| Diethylenetriamine | 3.0 | | |

TABLE VI-continued

|  | Amphoteric I | Amphoteric II | Amphoteric III |
|---|---|---|---|
| Diglycolamine | | 3.0 | |
| Polyethylenimine | | | 3.0 |
| Water | 65.5 | 65.5 | 65.5 |

These shampoos are prepared as described in Example 8. The visual observations of these shampoo systems are recorded in Table VII.

TABLE VII

| Experimental Conditions | Observations | | |
|---|---|---|---|
|  | DETA | DGA | PEI-1000 |
| pH - unadjusted Visual - unadjusted | 10.1 Crystal clear solution | 9.6 Yellow translucent liquid with heavy white precipitate | 9.1 Slightly cloudy solution with heavy white precipitate (smoky color solution) |
| pH adjustment with HCl | Shampoo remains clear down to approximately pH 9.3 (smoky color), slight degree of white precipitation, between pH 9.0 to 8.5 (with cloudy grey colored solution). | Yellow translucent liquid with heavy white precipitate remains (pH 8.5). | Grey translucent liquid with heavy white precipitate (pH 8.5) |
| pH adjusted with NaOH | Clear soluble solution remains throughout | A significant portion of zinc pyridinethione doesn't begin to solubilize until above pH 12.0 (yellow solution) | A significant portion of zinc pyridinethione doesn't begin to solubilize until above pH 12.0 (yellow solution) |

From the results of the experiments disclosed in Tables V and VII, it is evident that the aliphatic polyamines such as diethylene triamine are effective solubilizing agents for heavy metal salts of pyridinethione and they are far superior to the prior art suggestions such as diglycolamine and pyridinethione. Only the aliphatic polyamines are effective solubilizers in the pH range suitable for toilet and household products such as shampoos and textile treating compositions.

The following examples illustrate other compositions which make use of the present invention. These examples are merely illustrative and do not limit the scope of use of the invention.

Example 12
Hair Groomer

|  | Percent by Weight |
|---|---|
| Ethanol | 70 |
| Isopropyl myristate | 10 |
| Zinc pyridinethione | 2 |
| Diethylene triamine | 3.5 |
| Perfume | 0.4 |
| Water | 14.1 |
|  | 100.0 |

Example 13
Phytotoxic Agent

|  | Percent by Weight |
|---|---|
| Zinc pyridinethione | 10.0 |
| Diethylene triamine | 20.0 |
| Water | 70.0 |
|  | 100.0 |

This composition is bactericidal for a variety of bacteria such as *Staph. aureus*, *Staph. albus*, *E. coli*, to mention a few.

Example 14
Textile Treating Composition

|  | Percent by Weight |
|---|---|
| Sodium tridecylbenzene sulfonate | 10 |
| Sodium lauryl polyethoxamer sulfate (average of 5 ethylene oxide groups) | 3 |
| Lauric-myristic (70:30) isopropanolamide | 2.5 |
| Lauric-myristic (70:30) diethanolamide | 2.5 |
| Sodium xylene sulfonate | 8.6 |
| Potassium pyrophosphate | 15.0 |
| Zinc pyridinethione | 2.5 |
| Diethylene triamine | 5.0 |
| Water | 50.9 |
|  | 100.0 |

Example 15
Diaper Treating Composition

|  | Percent by Weight |
|---|---|
| Glycerine | 15 |
| Zinc pyridinethione | 0.5 |
| Diethylene triamine | 0.5 |
| Perfume | 0.5 |
| Water | 83.5 |
|  | 100.0 |

The pH of any of the above solutions may be adjusted by mineral and organic acids such as hydrochloric, sulfuric, citric, oxalic, tartaric, maleic and malic and alkalies such as sodium hydroxide, potassium hydroxide and ammonium hydroxide.

Although the present invention has been described with reference to particular embodiments and examples, in particular the use of the preferred solubilizer (diethylene triamine), preferred heavy metal salt of pyridinethione (zinc pyridinethione) and preferred solvent (water) in most of the examples, it will be apparent to those skilled in the art that similar results may be obtained with the other ingredients disclosed and their equivalents.

What is claimed is:

1. A clear liquid composition for use as a bactericide or fungicide consisting essentially of ¼ to 20% by weight of the zinc salt of 1-hydroxy-2-pyridinethione, an aliphatic polyamine having the general formula
$$H_2N[CH_2CH_2NH]_nH$$
wherein $n$ represents a number from 1 to 5, the weight ratio of said amine to said pyridinethione salt being from about ½ to 1 to about 5 to 1, and the balance being a solvent selected from the group consisting of water, $C_2$-$C_3$ monohydric alcohols, $C_2$-$C_3$ polyhydric alcohols, dimethyl formamide, dimethylacetamide, dimethylsulfoxide and mixtures thereof.

2. A clear liquid composition in accordance with claim 1 wherein said solvent is a mixture of water and a $C_2$-$C_3$ monohydric or polyhydric alcohol.

3. A clear liquid composition in accordance with claim 1 wherein said solvent is ethanol.

4. A clear liquid composition in accordance with claim 1 wherein said polyamine is diethylene triamine and the ratio of said polyamine to said pyridinethione salt is about 1 to 1 to about 2 to 1.

5. A method of solubilizing the zinc salt of 1-hydroxy-2-pyridinethione for use as a bactericide or fungicide in a solvent selected from the group consisting of water, $C_2$-$C_3$ monohydric alcohols, $C_2$-$C_3$ polyhydric alcohols, dimethyl formamide, dimethylacetamide, dimethylsulfoxide and mixtures thereof which consists essentially of the step of solubilizing said pyridinethione salt in said solvent by admixing with an aliphatic polyamine having the general formula $H_2N_7[CH_2CH_2NH_7]_nH$ wherein $n$ represents a number from 1 to 5, said pyridinethione salt being ¼ to 20% by weight of the resulting solution and the weight ratio of said aliphatic polyamine to said pyridinethione salt being from about ½ to 1 to about 5 to 1 and sufficient to improve the solubility of said pyridinethione salt.

6. A method in accordance with claim 5 wherein said solvent is a mixture of water and a $C_2$-$C_3$ monohydric or polyhydric alcohol.

7. A method in accordance with claim 5 wherein said solvent includes water and the pH of said solution is about 9.

8. A method in accordance with claim 5 wherein said solvent is ethanol.

9. A method in accordance with claim 5 wherein said aliphatic polyamine is diethylene triamine.

* * * * *